(12) United States Patent
Klausener et al.

(10) Patent No.: US 6,740,761 B2
(45) Date of Patent: May 25, 2004

(54) PROCESS FOR PREPARING 2-ALKYL-3ARYL-AND-HETEROARYLOXAZIRIDINES AND NOVEL 2-ALKYL-3-ARYLOXAZIRIDINES

(75) Inventors: Alexander Klausener, Pulheim (DE); Reinhard Langer, Tönisvorst (DE); Stephan Ratsch, Solingen (DE); Michael Dockner, Köln (DE)

(73) Assignee: Bayer Aktiengesellschaft, Leverkusen (DE)

( * ) Notice: Subject to any disclaimer, the term of this patent is extended or adjusted under 35 U.S.C. 154(b) by 0 days.

(21) Appl. No.: 09/899,421

(22) Filed: Jul. 5, 2001

(65) Prior Publication Data

US 2002/0111339 A1 Aug. 15, 2002

(30) Foreign Application Priority Data

Jul. 7, 2000 (DE) .......................... 100 33 079

(51) Int. Cl.[7] ............................ C07D 273/01
(52) U.S. Cl. ....................................... 548/959
(58) Field of Search ......................... 548/959

(56) References Cited

U.S. PATENT DOCUMENTS 2,784,182 A * 3/1957 Krimm et al. .............. 260/239
3,819,653 A * 6/1974 Schirmann et al. ......... 260/333

FOREIGN PATENT DOCUMENTS

| EP | 0 217 269 | 8/1990 |
| GB | 743940 | 1/1956 |
| WO | 00/02848 | 1/2000 |

OTHER PUBLICATIONS

Bulachkova Al, et al. Preparation of oxaziridines under conditions of phase–transfer catalysts. Zh Org Khim. 1990;26:216 (English abstract provided).*

J. Chem. Soc. Perkin Trans., 1, (month unavailable) 1990, pp. 301–306, Derek R. Boyd, Peter B. Coulter, M. Rosaleen McGucking, Narain D. Sharma, W. Brian Jennings and Valerie E. Wilson, "Imines and Derivatives. Part 24. Nitrone Synthesis by Imine Oxidation using either a Peroxyacid or Dimethyldioxirane".

Tetrahedron Letters, No. 28, (month unavailable) 1974, pp. 2453–2456, T. Polonski and A. Chimiak, "Oxidation of Amino Acid Esters Into N–Hydroxyamino Acid Derivatives".

J. Am. Chem. Soc., vol. 79, Oct.–Dec. 1957, p. 5749, "Preparation and Properties of Oxaziranes".

J. Chem. Soc. Perkin Trans. 1, (month unavailable) 1990, Toru Minami, Kazunari Hirakawa, Shinichiro Koyanagi, Seigo Nakamura and Masahiko Yamaguchi, "A New Synthesis of α–Methylene Lactones".

Kloc, K. et al: "Synthesis of 2–alkyl–3–aryloxaziridines" Synthesis, Nr. 12, Dec. 1987, Seiten 1084–1087, XP002180898.

* cited by examiner

*Primary Examiner*—Deborah C. Lambkin
*Assistant Examiner*—Golam M M Shameem
(74) *Attorney, Agent, or Firm*—Godfried R. Akorii; Diderico van Eyl

(57) ABSTRACT

2-Alkyl-3-aryl- or -heteroaryloxaziridines are prepared in a particularly advantageous manner by oxidizing corresponding N-alkyl-aryl- or -heteroarylaldimines with an aromatic percarboxylic acid or a salt thereof in the presence of water, a water-soluble base, and a water-miscible solvent, at temperatures below 30° C. Using this method, it is also possible to obtain novel 2-alkyl-3-aryloxaziridines.

9 Claims, No Drawings

PROCESS FOR PREPARING 2-ALKYL-3ARYL-AND-HETEROARYLOXAZIRIDINES AND NOVEL 2-ALKYL-3-ARYLOXAZIRIDINES

BACKGROUND OF THE INVENTION

The present invention relates to an improved process for preparing 2-alkyl-3-aryl- and -heteroaryloxaziridines by oxidation of the corresponding aryl- or heteroarylaldimines using a peroxy compound.

2-tert-Butyl-3-phenyloxaziridine, for example, serves as starting material for preparing N-(tert-butyl)hydroxylamine, which is used for the synthesis of pharmaceutically active compounds.

It is already known (J. Am. Chem. Soc., 79, 5749 (1957)), that arylaldimines containing an unsubstituted or a nitro-substituted phenyl group can be covered with anhydrous peracetic acid into the corresponding oxaziridine which can be isolated by distillation and then hydrolyzed using aqueous-methanolic sulfuric acid, giving, after addition of alkali, the corresponding free N-alkylated hydroxylamine. The anhydrous peracetic acid required is prepared in situ from 90% strength aqueous hydrogen peroxide using excess acetic anhydride and catalytic amounts of sulfuric acid, in the solvent methylene chloride. The handling of such concentrated hydrogen peroxide solutions is associated with extremely high safety expenditure. Thus, if in any way possible, the preparation and handling of large amounts of such hydrogen peroxide solutions are avoided.

EP-B 217,269 discloses that N-alkyl-substituted aryloxaziridines are obtainable by reacting arylaldimines with perpropionic acid in benzene. To prevent hydrolysis of the arylaldimines and the aryloxaziridines under the acidic reaction conditions, the water content of the perpropionic acid has to be less than 0.1% by weight ("anhydrous perpropionic acid"). The preparation and handling of anhydrous perpropionic acid, too, is a process which requires high safety expenditure, in particular during the azeotropic distillation to remove the water.

Commercial m-chloroperbenzoic acid is a solid and, accordingly, easier to handle than peracetic acid or perpropionic acid. m-Chloroperbenzoic acid, too, has been used for oxidizing arylaldimines (J. Chem. Soc. Perkin Trans. 1 1990, 301 and 2390), the reaction being carried out in methylene chloride or methanol, i.e. a non-aqueous medium.

It is also known that benzylideneamino acid esters can be oxidized to the corresponding oxaziridines using monoperphthalic acids in the solvent diethyl ether (Tetrahedron Lett., 28, 2453 (1994)).

In general, the preparation and handling of percarboxylic acids is safer if water is present during their preparation and use, for example during oxidations. However, in the presence of acids and water, imines generally tend to hydrolyze. This is the reason why the presence of water has been substantially excluded in the known imine oxidations.

Furthermore, the presence of acid and water in the reaction medium used for preparing oxaziridines promotes hydrolytic cleavage of the oxaziridines formed into the corresponding aldehyde and the corresponding N-substituted hydroxylamine. The latter for its part is readily oxidized by the percarboxylic acid present to give the corresponding nitroso compound. Nitroso compounds are known to be substances which are highly carcinogenic. Accordingly, they have to be excluded in the preparation of intermediates for pharmaceutically active compounds.

According to WO 00/02848, the problem of the hydrolysis and the formation of undesirable subsequent products is solved by carrying out the oxidation with m-chloroperbenzoic acid in a two-phase system of toluene and an aqueous sodium carbonate solution. However, such a procedure is not recommended for realizing an industrial process, since two-phase reaction systems lead to upscaling problems which, if at all, can only be solved with great efforts.

None of the known methods for preparing aryloxaziridines by oxidizing arylamines with percarboxylic acids are satisfactory for industrial-scale processes. Accordingly, there is still a need for a simple, economical and low-risk process for preparing 2-alkyl-3-aryl- and heteroaryloxaziridines.

SUMMARY OF THE INVENTION

This invention, accordingly, provides a process for preparing 2-alkyl-3-aryl- and heteroaryloxaziridines comprising oxidizing corresponding N-alkyl-aryl- or -heteroarylaldimines with an aromatic percarboxylic acid or a salt thereof in the presence of water, a water-soluble base, and a water-miscible solvent, at temperatures below 30° C.

DETAILED DESCRIPTION OF THE INVENTION

Suitable N-alkyl-aryl- and -heteroarylaldimines are, for example, those of the formula (I)

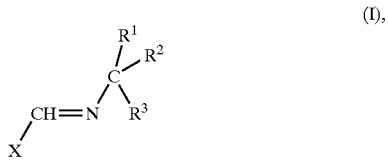

in which $R^1$, $R^2$, and $R^3$ independently of one another each represent hydrogen, straight-chain or branched $C_1$–$C_{20}$-alkyl, $C_3$–$C_8$-cycloalkyl, straight-chain or branched $C_2$–$C_{10}$-alkenyl, or $C_6$–$C_{10}$-aryl, or the entire $C(R^1)(R^2)(R^3)$ group represents a $C_3$–$C_8$-cycloalkyl radical, and X represents $C_6$–$C_{12}$-aryl or heteroaryl having 4 or 5 C atoms and 1 or 2 identical or different heteroatoms selected from the group consisting of N, O and S, wherein all alkyl, cycloalkyl, alkenyl, aryl, and heteroaryl radicals may optionally be mono- or polysubstituted (alkyl radicals, for example, by saturated $C_3$–$C_{12}$-cycloalkyl, $C_6$–$C_{10}$-aryl, $C_2$–$C_8$-alkenyl, fluorine, chlorine, bromine, iodine, hydroxyl, $C_1$–$C_6$-alkoxy, $C_6$–$C_{10}$-aryloxy, carboxyl, $C_1$–$C_6$-alkoxycarbonyl, nitro, amido, nitrile, sulfonyl, or phosphate, and cycloalkyl, alkenyl, aryl, and heteroaryl radicals, for example, by $C_1$–$C_6$-alkyl, fluorine, chlorine, bromine, hydroxyl, $C_1$–$C_6$-alkoxy, carboxyl, $C_1$–$C_6$-alkoxycarbonyl, nitro, sulfonyl, or nitrile).

Preferred alkenyl radicals are those having electron-depleted double bonds, and preferred heteroaryl radicals are those which only contain the heteroatom(s) oxygen.

If N-alkyl-aryl- or -heteroarylaldimines of the formula (I) are used, the corresponding 2-alkyl-3-aryl- or -heteroaryloxaziridines of the formula (II)

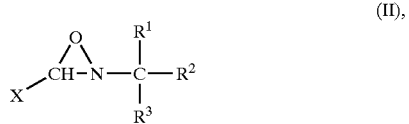

in which the symbols used are as defined under formula (I), are obtained.

In the formulas (I) and (II), $R^1$, $R^2$, and $R^3$, preferably independently of one another, each represent hydrogen, straight-chain or branched $C_1$–$C_{10}$-alkyl, $C_3$–$C_6$-cycloalkyl, straight-chain or branched $C_2$–$C_6$-alkenyl, or phenyl, or the entire $C(R^1)(R^2)(R^3)$ group represents $C_3$–$C_6$-cycloalkyl, the radicals mentioned not being substituted any further.

In the formulas (I) and (II), X preferably represents phenyl, naphthyl, or furyl, where the phenyl and naphthyl radicals may optionally be substituted by one or two identical or different radicals from the group consisting of $C_1$–$C_6$-alkyl, fluorine, chlorine, bromine, hydroxyl, $C_1$–$C_6$-alkoxy, $C_1$–$C_6$-alkoxycarbonyl, nitro, sulfonyl, and nitrile.

In the formulas (I) and (II), the entire $C(R^1)(R^2)(R^3)$ group particularly preferably represents unsubstituted n-propyl, n-butyl, iso-butyl, t-butyl, n-pentyl, cyclopropyl, cyclopentyl, or cyclohexyl, and X particularly preferably represents 4-methoxyphenyl, 4-methylphenyl, 4-chlorophenyl, or 4-nitrophenyl.

Particularly suitable aromatic percarboxylic acids and salts thereof are m-chloroperbenzoic acid and monoperoxyphthalic acid and their alkali metal and magnesium salts. Preference is given to using the magnesium salt of monoperoxyphthalic acid.

Suitable water-soluble bases are, for example, alkali metal and alkaline earth metal oxides, hydroxides, carbonates, bicarbonates, hydrogen phosphates, and dihydrogen phosphates. Preference is given to using sodium carbonate or sodium bicarbonate.

Suitable water-miscible solvents are, for example, water-miscible organic solvents that are inert under the reaction conditions, for example, mono- and polyhydric alcohols having up to 6 C atoms. Preference is given to using methanol or ethanol.

The process according to the invention can be carried out by initially preparing a mixture of the N-alkyl-aryl- or -heteroaryl aldimine and the water-miscible solvent. The aldimine content in the solvent can be varied within a relatively wide range. The concentration of the aldimine in the mixture with the solvent can, for example, be from 5 to 80% by weight, preferably from 20 to 50% by weight and in particular from 35 to 40% by weight.

This mixture can then be treated with an aqueous solution of the base, for example, at from 0 to 30° C. This operation is preferably carried out at from 10 to 25° C. The concentration of the base in water can be varied as desired and may, for example, be from 15 to 30% by weight. Preference is given to solutions having a strength of from 15 to 25% by weight. Secondary and tertiary amines can also be used as such, i.e., without water. However, the amount of the base should preferably be kept within narrow limits. Based on one mole of the aldimine, for example, 0.09 to 2 equivalents of base may be employed. Preference is given to using from 0.9 to 1.2 equivalents of base, in particular from 1.0 to 1.1 equivalents of base.

A solution of the aromatic percarboxylic acid or its salt in water can be added to the resulting mixture. The addition rate is chosen such that, in spite of the heat of reaction to be dissipated, the reaction temperature does not exceed 30° C. The lower limit for the reaction temperature may, for example be 0° C. Preference is given to reaction temperatures in the range from 10 to 25° C. Based on 1 mol of the aldimine, it is possible to use, for example, from 0.9 to 1.2 equivalents of active oxygen in the form of the aromatic percarboxylic acid or its salts. This amount is preferably from 0.95 to 1.05 equivalents. Frequently, the aromatic percarboxylic acid or its salt is not commercially available as 100% pure material. Even aromatic percarboxylic acids and their salts which are not 100% pure are suitable for the process according to the invention. Preference is given to using aromatic percarboxylic acids and the salts thereof having a content of at least 80%.

The concentration of the solution of the aromatic carboxylic acid or its salts in water can, for example, be from 1 to 20% by weight. It is preferably from 15 to 20% by weight.

After the addition of the aqueous solution of an aromatic percarboxylic acid or the salts thereof has ended, the reaction mixture can be stirred at, for example, from 5 to 30° C. (preferably at from 15 to 25° C.) until it has been established, for example, by gas chromatography, that the reaction has ended. The end of the reaction is defined as the point where at most 0.5 area % of the starting material can be detected by gas chromatography. In general, this is the case after 2 to 3 hours.

To work up the reaction mixture, it is frequently sufficient to switch off the stirrer, whereupon the mixture separates into two phases, an upper product phase and a lower aqueous phase. The 2-alkyl-3-aryl- or -heteroaryloxaziridine prepared can then be obtained by phase separation.

In some cases, phase separation of the reaction mixture is difficult, for example, if mixed phases are obtained or if the aromatic percarboxylic acid or its salt used contained additives (for example, stabilizers) that counteract phase separation. In the case of sludge-like phases, for example, it is frequently possible to obtain, by filtration, a filtrate where phase separation occurs more readily. In other cases, aromatic percarboxylic acids or salts thereof that do not contain any additives that interfere with phase separation should be used, or an extractive method should be used to work up the reaction mixture.

It is also possible to obtain the product by extraction from the reaction mixture using an organic solvent, followed by distillative removal of the solvent from the extract. For the extraction, it is possible to use, for example, saturated or unsaturated hydrocarbons or halogenated, saturated or unsaturated hydrocarbons. Preference is given to using petroleum ether, toluene, methylene chloride, and chlorobenzene.

The product, which can be isolated in a yield of about 80% of theory (based on 100% 2-alkyl-aryl- or -heteroaryloxazilidine) may contain, as impurities, traces of the starting material and the water-miscible solvent used, in addition to benzaldehyde.

The process according to the invention can be carried out in a simple manner; if the stated reaction conditions are adhered to, there are no particular problems with respect to safety, the obtainable yields are good, no undesirable by-products are formed, and upscaling problems can be solved without particular efforts. It was unexpected that the product according to the invention gives such good results since, as discussed at the outset, it had to be expected that the oxaziridine formed would be cleaved under the reaction conditions and that undesirable by-products would be formed.

The present invention furthermore relates to the novel compounds 2-isopropyl-3-(4-methoxyphenyl)oxaziridine and 2-n-propyl-3-(4-methoxy-phenyl)oxaziridine. The way in which they can be prepared is described above. They give access to the corresponding hydroxylamines and thus to novel synthesis building blocks for pharmaceutically active compounds.

The following examples further illustrate details for the process of this invention. The invention, which is set forth in the foregoing disclosure, is not to be limited either in spirit or scope by these examples. Those skilled in the art will readily understand that known variations of the conditions of the following procedures can be used. Unless otherwise noted, all temperatures are degrees Celsius and all percentages are percentages by weight.

EXAMPLES

Example 1

In a 2 liter double-jacketed ground-glass beaker with outlet at the bottom, glass stirrer, temperature sensor, dropping funnel, and condenser, 140.6 g of N-(tert-butyl) benzaldimine and 222.3 g of methanol were initially charged at room temperature. Within 30 minutes, 523.4 g of a 17% by weight strength aqueous sodium carbonate solution were added dropwise to the solution, at an internal temperature of from 18 to 22° C. After the addition had ended, the jacket temperature of the reactor was adjusted to 15° C. using a thermostat. Once this temperature had been reached, 1323.1 g of magnesium monoperoxyphthalate hexahydrate in the form of a freshly prepared 20% by weight strength aqueous solution, divided into two equal portions, were metered in within one hour. During the addition, checks were made to ensure that the internal temperature did not exceed 23° C. The resulting emulsion was stirred at an internal temperature of from 22 to 23° C. and a jacket temperature of 20° C. for 3 hours. The stirrer was then switched off, and after one hour and twenty minutes the upper product phase was separated from the lower aqueous phase. This gave 129.6 g of a yellow liquid. This corresponds to a crude yield of 85.6% of theory of 2-tert-butyl-3-phenyl-oxaziridine. Gas chromatographic analysis of the isolated product showed:

| 2-tert-butyl-3-phenyloxaziridine: | 95.9 area % |
|---|---|
| N-(tert-butyl)benzaldimine: | 0.2 area % |
| benzaldehyde: | 3.5 area %. |

According to $^1$H-NMR analysis, the content of 2-tert-butyl-3-phenyl-oxaziridine in the isolated product was 92.2% by weight.

Example 2

In a multi-necked flask fitted with stirrer, thermometer, dropping funnel, and condenser, 17.7 g of N-(isopropyl)-4-methoxybenzaldimine and 25.7 g of methanol were initially charged at room temperature. Within 35 minutes, 62.4 g of a 17% by weight strength aqueous sodium carbonate solution were added dropwise to the solution, at an internal temperature of 18–22° C. Within one hour, 155.0 g of magnesium monoperoxyphthalate hexahydrate were metered in in the form of a 20% by weight strength aqueous solution, divided into two equal portions. Using an ice/water bath, it was ensured that the internal temperature did not exceed 23° C. The mixture was stirred at from 22 to 23° C. for 3 hours. The reaction mixture was extracted with 200 ml of methylene chloride and the solvent was then removed under reduced pressure, giving 17.8 g of 2-isopropyl-3-(4-methoxyphenyl)oxaziridine. This corresponds to a yield of 92%.

$^1$H-NMR (400 MHz, CDCl$_3$): δ 1.15 (3H, d, J 6 Hz, CH$_3$-iPr), 1.31 (3H, d, J 6 Hz, CH$_3$-iPr), 2.25–2.39 (1H, m, CH-iPr), 3.79 (3H, s, CH$_3$O), 4.45 (0.9H, s, E-isomer), 5.22 (0.1H, s, Z-isomer), 6.89 (2H, d, J 10 Hz, Ar—H), 7.35 (2H, d, J 10 Hz, Ar—H).

Example 3

In a multi-necked flask fitted with stirrer, thermometer, dropping funnel and condenser, 46.6 g of N-(propyl)-4-methoxybenzaldimine and 64.3 g of methanol were initially charged at room temperature. 156.3 g of a 17% by weight strength aqueous sodium carbonate solution were added dropwise to the solution, at an internal temperature of 18–22° C. Within one hour, 387.2 g of magnesium monoperoxyphthalate hexahydrate were metered in in the form of a 20% by weight strength aqueous solution, divided into two equal portions. Using an ice/water bath, it was ensured that the internal temperature did not exceed 23° C. The mixture was stirred at from 22 to 23° C. for 3 hours. The reaction mixture was extracted with 400 ml of methylene chloride and the organic phase was then dried with magnesium sulfate and the solvent was then removed under reduced pressure. This gave 46.9 g of 2-n-propyl-3-(4-methoxyphenyl)oxaziridine. This corresponds to a yield of 97%.

$^1$H-NMR (400 MHz, CDCl$_3$): δ 1.00 (3H, t, J 9 Hz, CH$_3$—Pr), 1.67–1.83 (2H, m, CH$_2$—Pr), 2.64–2.77 (1H, m, CH$_2$—Pr), 2.83–2.97 (1H, m, CH$_2$—Pr), 3.80 (3H, s, CH$_3$O), 4.44 (1H, s, E-isomer), 5.20 (0.1H, s, Z-isomer), 6.89 (2H, d, J 10 Hz, Ar—H), 7.33 (2H, d, J 10 Hz, Ar—H).

Example 4

In a multi-necked flask fitted with stirrer, thermometer, dropping funnel, and condenser, 19.2 g of N-(propyl)-4-nitrobenzaldimine and 90 g of methanol were initially charged at room temperature. 62.4 g of a 17% by weight strength aqueous sodium carbonate solution were added dropwise to the solution, at an internal temperature of 18–22° C. Within one hour, 155.0 g of magnesium monoperoxyphthalate hexahydrate were metered in in the form of a 20% by weight strength aqueous solution, divided into two equal portions. Using an ice/water bath, it was ensured that the internal temperature did not exceed 23° C. The mixture was stirred at from 22 to 23° C. for 5 hours. The reaction mixture was extracted with 250 ml of methylene chloride and the organic phase was then washed twice with in each case 100 ml of water and then dried with magnesium sulfate, and the solvent was removed under reduced pressure. This gave 20.4 g of 2-n-propyl-3-(4-nitrophenyl)oxaziridine. This corresponds to a yield of 98%.

$^1$H-NMR (400 MHz, CDCl$_3$): δ 1.03 (3H, t, J 9 Hz, CH$_3$—Pr), 1.70–1.86 (2H, m, CH$_2$—Pr), 2.67–2.81 (1H, m, CH$_2$—Pr), 2.92–3.10 (1H, m, CH$_2$—Pr), 4.60 (0.9H, s, E-isomer), 5.32 (0.1H, s, Z-isomer), 7.60 (2H, d, J 10 Hz, Ar—H), 8.22 (2H, d, J 10 Hz, Ar—H).

What is claimed is:

1. A process for preparing a 2-alkyl-aryl- or -heteroaryloxaziridine comprising oxidizing a corresponding N-alkyl-aryl- or -heteroarylaldimine with an aromatic percarboxylic acid or a salt thereof in the presence of water, a water-soluble base, and a water-miscible solvent, at temperatures below 30° C.

2. A process according to claim 1 wherein an N-alkyl-aryl- or -heteroarylaldimine of the formula (I)

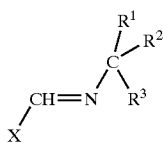

(I), wherein
R$^1$, R$^2$, and R$^3$ independently of one another each represent hydrogen, straight-chain or branched C$_1$–C$_{20}$-alkyl, C$_3$–C$_8$-cycloalkyl, straight-chain or branched C$_2$–C$_{10}$-alkenyl, or C$_6$–C$_{10}$-aryl, or the entire C(R$^1$)(R$^2$)(R$^3$) group represents a C$_3$–C$_8$-cycloalkyl radical, and X represents C$_6$–C$_{12}$-aryl or heteroaryl having 4 or 5 C atoms and 1 or 2 identical or different heteroatoms selected from the group consisting of N, O, and S, wherein all alkyl, cycloalkyl, alkenyl, aryl, and heteroaryl radicals may optionally be mono- or polysubstituted, is oxidized to form the corresponding 2-alkyl-3-aryl- or -heteroaryloxaziridines of the formula (II)

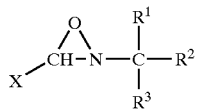

(II), in which R$^1$, R$^2$, R$^3$, and X are as defined for formula (I).

3. A process according to claim 2 wherein one or more alkyl radicals are mono- or polysubstituted by saturated C$_3$–C$_{12}$-cycloalkyl, C$_6$–C$_{10}$-aryl, C$_2$–C$_8$-alkenyl, fluorine, chlorine, bromine, iodine, hydroxyl, C$_1$–C$_6$-alkoxy, C$_6$–C$_{10}$-aryloxy, carboxyl, C$_1$–C$_6$-alkoxycarbonyl, nitro, amido, nitrile, sulfonyl, or phosphate and wherein one or more cycloalkyl, alkenyl, aryl, and heteroaryl radicals are mono- or polysubstituted by C$_1$–C$_6$-alkyl, fluorine, chlorine, bromine, hydroxyl, C$_1$–C$_6$-alkoxy, carboxyl, C$_1$–C$_6$-alkoxycarbonyl, nitro, sulfonyl, or nitrile.

4. A process according to claim 2 wherein in formulas (I) and (II),

R$^1$, R$^2$, and R$^3$ independently of one another each represent hydrogen, straight-chain or branched C$_1$–C$_{10}$-alkyl, C$_3$–C$_6$-cycloalkyl, straight-chain or branched C$_3$–C$_6$-alkenyl, or phenyl or the entire C(R$^1$)(R$^2$)(R$^3$) group represents C$_3$–C$_6$-cycloalkyl, wherein the radicals are not substituted any further, and X represents phenyl, naphthyl, or furyl, wherein the phenyl and naphthyl radicals may optionally be substituted by one or two identical or different radicals selected from the group consisting of C$_1$–C$_6$-alkyl, fluorine, chlorine, bromine, hydroxyl, C$_1$–C$_6$-alkoxycarbonyl, nitro, sulfonyl, and nitrile.

5. A process according to claim 1 wherein the percarboxylic acid or the salt thereof is m-chloroperbenzoic acid or monoperoxyphthalic acid or an alkali metal or magnesium salt thereof.

6. A process according to claim 1 wherein the water-soluble base is an alkali metal or alkaline earth metal oxide, hydroxide, carbonate, bicarbonate, hydrogen phosphate, or dihydrogen phosphate.

7. A process according to claim 1 wherein the water-miscible solvent is a mono- or polyhydric alcohol having up to 6 C atoms.

8. A process according to claim 2 comprising
(1) initially preparing a mixture comprising 5 to 80% by weight of the aldimine of the formula (I) in the water-miscible solvent,
(2) reacting the mixture with the aqueous solution comprising 15 to 30% by weight of a base,
(3) adding a 1 to 20% by weight strength solution of an aromatic percarboxylic acid or a salt thereof to the resulting mixture at such a rate that the reaction temperature does not exceed 30° C.,
(4) stirring the resulting mixture at from 5 to 30° C. until the reaction has ended, and
(5) working up the reaction mixture by phase separation or extraction.

9. A process according to claim 2 wherein, based on the aldimine of the formula (I), from 0.09 to 2 equivalents of base and from 0.9 to 1.2 equivalents of active oxygen in the form of an aromatic percarboxylic acid or salt thereof are used.

* * * * *